United States Patent
Nihira et al.

Patent Number: 5,861,534
Date of Patent: Jan. 19, 1999

[54] DIAMINOBENZENE DERIVATIVES AND POLYIMIDES PREPARED THEREFROM

[75] Inventors: Takayasu Nihira; Yoshio Miyamoto; Hideyuki Endo; Toyohiko Abe, all of Funabashi, Japan

[73] Assignee: Nissan Chemical Industries, Ltd., Tokyo, Japan

[21] Appl. No.: 711,786

[22] Filed: Sep. 10, 1996

Related U.S. Application Data

[62] Division of Ser. No. 428,365, Apr. 25, 1995.

[30] Foreign Application Priority Data

Apr. 28, 1994 [JP] Japan ........................ 6-91845

[51] Int. Cl.⁶ ............... C07C 217/84; C07C 229/60; C07C 237/32
[52] U.S. Cl. .................. 564/305; 564/157; 564/167; 564/168; 564/443; 560/19; 560/45; 560/49; 546/167
[58] Field of Search ................... 564/305, 443

[56] References Cited

FOREIGN PATENT DOCUMENTS 3235615  3/1984  Germany ............... 564/305

OTHER PUBLICATIONS

Miller et al., Chemical Abstracts, vol. 123, abstract 56604, 1995.
Moeller et al., Chemical Abtracts, vol. 122, abstract 38518, 1995.
Rajappa et al., Chemical Abstracts, vol. 108, abstract 21887, 1988.
Waring, Chemical Abstracts, vol. 87, abstract 53249, 1977.
Beard et al., Chemical Abstracts, vol. 87, abstract 6028, 1977.

*Primary Examiner*—Richard L. Raymond
*Attorney, Agent, or Firm*—Oblon, Spivak, McClelland, Maier & Neustadt, P.C.

[57] ABSTRACT

A diaminobenzene derivative of the formula (I):

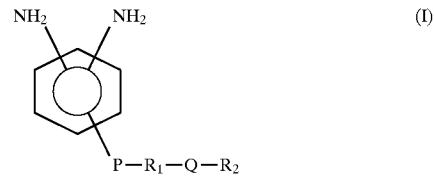

wherein each of P and Q which may be the same or different from each other, is a single bond, or a bivalent organic group selected from the group consisting of —O—, —COO— and —CONH—, $R_1$ is a $C_{2-22}$ straight chain alkylene group, and $R_2$ is a cyclic group selected from the group consisting of an aromatic ring, an aliphatic ring, a heterocyclic ring and substituted forms of such rings.

9 Claims, No Drawings

DIAMINOBENZENE DERIVATIVES AND POLYIMIDES PREPARED THEREFROM

This is a Division, of application Ser. No. 08/428,365, filed on Apr. 25, 1995; pending.

The present invention relates to novel diaminobenzene derivatives and polyimides prepared by using such derivatives as one of the starting materials. More particularly, it relates to diamines having substituents similar to liquid crystal molecules, which can readily be prepared on an industrial scale and polyimides having substituents similar to liquid crystal molecules, which can be prepared by using such diamines as one of the starting materials. The polyimides prepared by using the diamines of the present invention, are useful particularly for alignment films for liquid crystal display devices.

Heretofore, polyimides are widely used as protective materials or insulating materials in electric and electronic fields by virtue of their high mechanical strength, heat resistance and solvent resistance. However, developments in electric and electronic fields have been remarkable in recent years, and increasingly high levels of properties have been required for the materials to be used in such fields. Especially for alignment films for liquid crystal display devices, polyimides have heretofore been employed in most cases by virtue of the uniform quality and durability of the coated film surface. However, along with the trend for high densification and high performance of display devices, the surface properties of the polyimide coating films have become particularly important, and it has been necessary to impart new properties which conventional polyimides do not have.

Liquid display devices are display devices which utilize electrooptical changes of liquid crystals, and they are small in size and light in weight and have a feature that their power consumption is small. Accordingly, they have found remarkable developments in recent years as display devices for various displays. Among them, a twisted nematic type (TN type) electric field effect liquid crystal display device is a typical example wherein a nematic liquid crystal having a positive dielectric anisotropy is used, so that liquid crystal molecules are aligned in parallel with a pair of mutually opposing electrode substrates at the respective interfaces, and the two substrates are arranged so that the alignment directions of the respective liquid crystal molecules will cross each other.

In such a TN type liquid crystal display device, it is important to align liquid crystal molecules so that their axial directions will be uniformly in parallel with the surface of a substrate and so that the liquid crystal molecules will have a certain inclination angle (hereinafter referred to as a tilt angle) to the substrate. The following two methods are known as typical methods for aligning liquid crystal molecules in such a manner.

The first method is a method in which an inorganic substance such as silicon oxide is vapor-deposited obliquely to the substrate to form an inorganic film on the substrate, so that liquid crystal molecules are aligned in the direction of vapor deposition. This method is not efficient from the industrial point of view although it is thereby possible to attain stabilized alignment with a certain specific tilt angle.

The second method is a method wherein an organic coating film is formed on the surface of a substrate, and its surface is rubbed in a certain predetermined direction with a cloth of e.g. nylon or polyester, so that liquid crystal molecules are aligned in the direction of rubbing. By this method, it is possible to attain stabilized alignment relatively easily. Accordingly, this method is principally employed for industrial purpose. As the organic film, polyvinyl alcohol, polyoxyethylene, polyamide or polyimide may, for example, be used. However, the polyimide is most commonly used in view of the chemical stability, thermal stability, etc. However, the tilt angle obtainable by rubbing the polyimide is usually at a level of from 1 to 3° and it has been difficult to attain a larger tilt angle.

In the field of liquid crystal alignment films, it has been difficult to obtain a large tilt angle constantly by a method of rubbing an organic film of polyimide or the like. As a means to solve such a difficulty, Japanese Unexamined Patent Publication No. 297819/1987 proposes a treating agent for liquid crystal alignment which is composed of a reaction product of a long chain alkylamine with a polyimide precursor. Further, Japanese Unexamined Patent Publications No. 262527/1989 and No. 262528/1989 propose an agent for liquid crystal alignment which is composed of a mixture comprising a long chain alkyl compound and a polyimide precursor. Still further, Japanese Unexamined Patent Publication No. 25126/1989 proposes a treating agent for liquid crystal alignment which is composed of a polyimide prepared from a diamine having an alkyl group. Thus, many attempts have been made to increase the tilt angle of liquid crystal by introducing an alkyl group into a polyimide, and it has been possible to increase the tilt angle to some extent. On the other hand, however, there has been a new problem such that when an alkyl group is introduced into a polyimide, the polyimide surface tends to be water-repellent, whereby wettability of liquid crystal to the polyimide surface tends to be low. If the alkyl group is excessively introduced into a polyimide to increase the tilt angle, the wettability of liquid crystal tends to be low, and in an extreme case, failure in the liquid crystal alignment is likely to result. Consequently, the display performance of the liquid crystal display device tends to be poor.

Accordingly, it has been desired to develop a polyimide for alignment films whereby a large tilt angle can be obtained by rubbing and which provides adequate wettability with liquid crystal and excellent properties for alignment.

Depending upon the aligned states of their molecules, liquid crystals are classified into nematic, smectic and cholesteric. However, a common feature is that long axes of constituting molecules are aligned in parallel with one another. As prerequisites for a certain compound to exhibit a liquid crystal property from such a regular molecular alignment, there may be mentioned (1) that the molecular structure has a geometric shape suitable for the parallel alignment, and (2) that an intermolecular attraction sufficient to maintain the parallel alignment, is maintained. Because of these two prerequisites, a compound to exhibit a liquid crystal property is required to have a rod-like or a plate-like molecular shape, and further have a permanent dipole or a readily polarizable chemical bond group (functional group). Further, the type of a liquid crystal phase is said to be determined by a proper balance of the intermolecular attraction as between the terminals and between the side surfaces of such a rod-shaped molecule ("Most Recent Technology for Liquid Crystal" edited by Shoichi Matsumoto and Ichiyoshi Kakuta, p. 62, 1983, published by Kogyo Chosakai).

The present inventors have conducted extensive studies to improve the alignment property of liquid crystal by an alignment film for liquid crystal and as a result, have found that the alignment property of liquid crystal can be remarkably improved by introducing into the molecular structure of a polyimide a structure whereby an action corresponding to the intermolecular attraction effective among such liquid crystal molecules, can be maintained also between the polyimide of the alignment film and the liquid crystal molecules. The present invention has been accomplished on the basis of this discovery.

Thus, the present invention provides a diaminobenzene derivative of the formula (I):

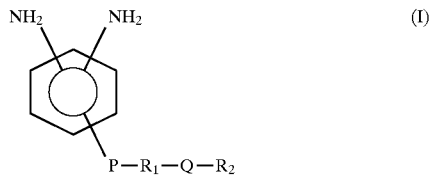
(I)

wherein each of P and Q which may be the same or different from each other, is a single bond, or a bivalent organic group selected from the group consisting of —O—, —COO— and —CONH—, $R_1$ is a $C_{2-22}$ straight chain alkylene group, and $R_2$ is a cyclic group selected from the group consisting of an aromatic ring, an aliphatic ring, a heterocyclic ring and substituted forms of such rings.

Further, the present invention provides a polyimide obtained by reacting a diamine containing at least one mol % of the diaminobenzene derivative of the formula (I), with a tetracarboxylic acid or its derivative to obtain a polyimide precursor having a reduced viscosity of from 0.05 to 5.0 dl/g (in N-methylpyrrolidone at 30° C., concentration: 0.5 g/dl) and subjecting the polyimide precursor to ring closure.

Now, the present invention will be described in detail with reference to the preferred embodiments.

The diaminobenzene derivative of the present invention can readily be synthesized and is useful as a starting material for a polyimide or a polyamide. Further, using such a derivative as one of starting materials, it is possible to obtain a polyimide having, on its side chain, a substituent similar to a liquid crystal molecule. Such a polyimide is useful particularly for an alignment film for a liquid crystal display device, and it is excellent in aligning liquid crystal to obtain a large tilt angle.

Except for discotic liquid crystal molecules, almost all of liquid crystal molecules have rod-shaped chemical structures, and they are composed of cyclic groups substituted by polar groups, which have a substantial degree of rigidity and which are called "cores" and linear alkyl groups ("Liquid Crystals-Fundamentals" coauthored by Mitsuharu Okano and Shinsuke Kobayashi, p. 179, 1985, published by Baiyukan).

The diaminobenzene derivative of the formula (I) of the present invention is a diamine having a structure similar to such a liquid crystal molecule, and it is composed of a diamine moiety of the formula:

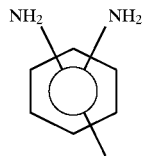

a spacer moiety of $R_1$, a cyclic group of $R_2$ and connecting moieties of P and Q. The process for its preparation is not particularly limited. However, it can be prepared, for example, by the following process.

In the synthesis of a diamine, it is common to prepare a corresponding dinitro compound of the formula (II)

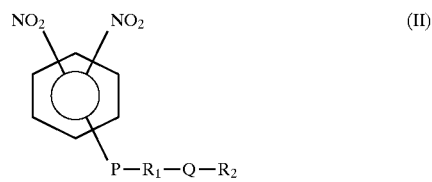
(II)

and further reduce the nitro groups by a conventional method to convert them to amino groups.

It is common to adopt a method wherein the dinitro moiety of the formula:

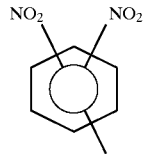

and the spacer moiety of $R_1$ are bonded by means of the connecting moiety of P, and then the cyclic group of $R_2$ is bonded thereto by means of the connecting moiety of Q, or a method wherein the cyclic group of $R_2$ and the spacer moiety of $R_1$ are firstly bonded by means of the connecting moiety of Q, and then the dinitro moiety is bonded by means of the connecting moiety of P.

Each of the connecting moieties of P and Q is a linking group such as a single bond, an ether bond of —O—, an ester bond of —COO— or an amide bond of —CONH—. Such linking groups can be formed by conventional methods for organic syntheses. For example, for the ether bond, it is common to employ a method wherein a corresponding halogen derivative is reacted with a hydroxyl group-substituted derivative in the presence of an alkali. For the ester bond, it is common to employ a method wherein a corresponding acid chloride is reacted with a hydroxyl group-substituted derivative in the presence of an alkali. Likewise, for the amide bond, it is common to employ a method wherein a corresponding acid chloride is reacted with an amino group-substituted derivative in the presence of an alkali.

A specific example of the starting material for forming the dinitro moiety is a dinitrobenzene substituted by a substituent for forming the connecting moiety of P, such as a halogen atom, a hydroxyl group or a halogenated acyl group. Specific examples of such a substituted dinitrobenzene include 2,3-dinitrobenzene, 2,4-dinitrobenzene, 2,5-dinitrobenzene, 2,6-dinitrobenzene, 3,4-dinitrobenzene and 3,5-dinitrobenzene. However, in view of the availability of the starting material and the reactivity for polyimide polymerization, it is most common to employ 2,4-dinitrochlorobenzene, 2,4-dinitrophenol or 2,4-dinitrobenzoic acid chloride.

The spacer moiety of $R_1$ is a straight chain alkylene group having a structure similar to a linear alkyl group forming a rod-shaped structure of a liquid crystal molecule. A specific example of the starting material for forming the spacer moiety of $R_1$ is a straight chain alkyl group having both ends substituted by substituents for forming the connecting moieties of P and Q, such as halogen atoms, hydroxyl groups, halogenated acyl groups or amino groups, and its carbon number is preferably optionally selected so that it corresponds to the linear alkyl group of the liquid crystal molecule. In view of the availability of the starting material and convenience for the synthetic reaction, it is most common to employ a $C_{2-22}$ straight chain alkylenediol, dihalide, diacyl halide, diamine, halogenated alcohol, amino alcohol, halogenated carboxylic acid, hydroxycarboxylic acid or aminocarboxylic acid.

The cyclic group of $R_2$ is a cyclic group having a structure similar to the cyclic compound forming the "core" moiety of a liquid crystal molecule. The cyclic compound forming such a "core" moiety may, for example, be the one wherein a plurality of 6-membered rings are directly connected, or they are connected by means of connecting groups. As the 6-membered rings, benzene rings, heterocyclic rings and cyclohexane rings may be mentioned as typical examples. Specific examples of such a cyclic group include a biphenyl ring, a terphenyl ring, a bicyclohexyl ring, a tercyclohexyl ring, a phenylcyclohexyl ring, a phenylpyridine ring, a cyclohexylpyridine ring, a phenyldioxane ring, a phenylpyrimidine, a cyclohexylpyrimidine ring, a phenylpyrazine ring, a cyclohexylpyrazine ring, as well as those wherein such cyclic compounds are connected by means of a connecting group such as ethylene, acetylene, an ester, oxymethylene, azo, azoxy or azomethine. For the cyclic group of $R_2$ of the present invention, such cyclic compounds and their analogues may be employed. However, in view of the availability of the starting material, easiness for the synthetic reaction, etc., it is preferred to employ a benzene ring, a cyclohexane ring, a biphenyl ring, a bicyclohexyl ring or a phenylcyclohexane ring.

The cyclic compound for forming the "core" moiety of a liquid crystal molecule is usually substituted by various terminal groups. As such terminal groups, a methyl group, an ethyl group, other alkyl groups, a halogen atom, a methoxy group, a trifluoromethoxy group, a nitro group, an amino group, a cyano group, an azo group, a formyl group, an acetyl group and an acetoxy group, are, for example, known. The cyclic group of $R_2$ of the present invention can be substituted by such substituents. In view of the availability of the starting material and easiness of the synthetic reaction, particularly preferred is a cyclic group substituted by a substituent selected from the group consisting of a halogen atom, a methoxy group, a trifluoromethoxy group, a cyano group and an alkyl group.

The starting material for forming the cyclic group of $R_2$ of the present invention may be the above-mentioned cyclic compound or a cyclic compound which corresponds to the above cyclic compound substituted by the above terminal group, which has a substituent for forming the connecting moiety of Q, such as a halogen atom, a hydroxyl group or a halogenated acyl group.

The diaminobenzene derivative of the formula (I) of the present invention obtainable by the above described process, can be poly-condensed with a tetracarboxylic acid or its derivative, such as a tetracarboxylic acid, a tetracarboxylic acid dihalide or a tetracarboxylic dianhydride to obtain a polyimide having on its side chain a substituent similar to a liquid crystal molecule.

A method for obtaining a polyimide of the present invention is not particularly limited. Specifically, a tetracarboxylic acid or its derivative may be reacted and polymerized with a primary diamine to form a polyimide precursor, which is then subjected to ring closure imide-conversion to obtain a polyimide.

The tetracarboxylic acid or its derivative to be used for the preparation of a polyimide of the present invention, is not particularly limited.

Specific examples include aromatic tetracarboxylic acids such as pyromellitic acid, 2,3,6,7-naphthalene tetracarboxylic acid, 1,2,5,6-naphthalene tetracarboxylic acid, 1,4,5,8-naphthalene tetracarboxylic acid, 2,3,6,7-anthracene tetracarboxylic acid, 1,2,5,6-anthracene tetracarboxylic acid, 3,3',4,4'-biphenyl tetracarboxylic acid, 2,3,3',4'-biphenyl tetracarboxylic acid, bis(3,4-dicarboxyphenyl)ether, 3,3',4,4'-benzophenone tetracarboxylic acid, bis(3,4-dicarboxyphenyl)sulfone, bis(3,4-dicarboxyphenyl)methane, 2,2-bis(3,4-dicarboxyphenyl)propane, 1,1,1,3,3,3-hexafluoro-2,2-bis(3,4-dicarboxyphenyl)propane, bis(3,4-dicarboxyphenyl)dimethylsilane, bis(3,4-dicarboxyphenyl)diphenylsilane, 2,3,4,5-pyridine tetracarboxylic acid and 2,6-bis(3,4-dicarboxyphenyl)pyridine, and their dianhydrides as well as their dicarboxylic acid diacid halides; alicyclic tetracarboxylic acids such as 1,2,3,4-cyclobutane tetracarboxylic acid, 1,2,3,4-cyclopentane tetracarboxylic acid, 1,2,4,5-cyclohexane tetracarboxylic acid, 2,3,5-tricarboxycyclopentylacetic acid and 3,4-dicarboxy-1,2,3,4-tetrahydro-1-naphthalenesuccinic acid, and their dianhydrides as well as their dicarboxylic acid diacid halides; and aliphatic tetracarboxylic acids such as 1,2,3,4-butane tetracarboxylic acid, and their dianhydrides as well as their dicarboxylic acid diacid halides.

For the application as alignment films, alicyclic tetracarboxylic acids and their dianhydrides as well as their dicarboxylic acid diacid halides are preferred from the viewpoint of the transparency of the coating films. Particularly preferred is 1,2,3,4-cyclobutanetetracarboxylic acid dianhydride.

Such tetracarboxylic acids and their derivatives may be used alone or in combination as a mixture of two or more of them.

In the present invention, a tetracarboxylic acid or its derivative, a diaminobenzene derivative of the formula (I) (hereinafter referred to simply as a diamine (I)) and other common diamine (hereinafter referred to simply as a common diamine) are copolymerized to obtain a polyimide having on its side chain a substituent similar to a liquid crystal molecule. Thus, the diamine to be used to obtain a polyimide of the present invention contains the diamine (I) as an essential component.

The common diamine other than the diamine (I) is a primary diamine which is commonly used for the synthesis of a polyimide, and it is not particularly limited. Specific examples of such a common diamine include aromatic diamines such as p-phenylenediamine, m-phenylenediamine, 2,5-diaminotoluene, 2,6-diaminotoluene, 4,4'-diaminobiphenyl, 3,3'-dimethyl-4,4'-diaminobiphenyl, 3,3'-dimethoxy-4,4'-diaminobiphenyl, diaminodiphenylmethane, diaminodiphenyl ether, 2,2'-diaminodiphenylpropane, bis(3,5-diethyl-4-aminophenyl)methane, diaminodiphenylsulfone, diaminobenzophenone, diaminonaphthalene, 1,4-bis(4-aminophenoxy)benzene, 1,4-bis(4-aminophenyl)benzene, 9,10-bis(4-aminophenyl)anthracene, 1,3-bis(4-aminophenoxy)benzene, 4,4'-bis(4-aminophenoxy)diphenylsulfone, 2,2'-bis[4-(4-aminophenoxy)phenyl]propane, 2,2-bis(4-aminophenyl)hexafluoropropane and 2,2-bis[4-(4-aminophenoxy)phenyl]hexafluoropropane; alicyclic diamines such as bis(4-aminocyclohexyl)methane and bis(4-amino-3-methylcyclohexyl)methane; and aliphatic diamines such as tetramethylene diamine and hexamethylene diamine, as well as diaminosiloxanes of the formula:

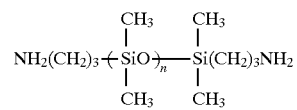

wherein n is an integer of from 1 to 10.

These diamines may be used alone or in combination as a mixture of two or more of them.

By adjusting the molar ratio of the diamine (I) to the total molar amount of the diamine used at the time of polymerization to obtain a polyimide of the present invention, it is possible to modify the surface properties, such as water repellency, of the polyimide, and further, when such a polyimide is used as a liquid crystal alignment film, it is possible to improve the wettability with the liquid crystal and to increase the tilt angle of the liquid crystal. In such a case, the molar ratio of the diamine (I) to the total molar amount of the diamine used, is at least one mol %, preferably at least 5 mol %.

A tetracarboxylic acid or its derivative is reacted and polymerized with the diamine (I) and the common diamine to form a polyimide precursor, which is then subjected to ring closure imide-conversion. Here, it is common to employ a tetracarboxylic acid dianhydride as the tetracarboxylic acid or its derivative. The ratio of the molar amount of the tetracarboxylic acid dianhydride and the total molar amount of the diamine (I) and the common diamine is preferably from 0.8 to 1.2. Like in a usual polycondensation reaction, the closer the molar ratio to 1, the larger the polymerization degree of the resulting polymer.

If the polymerization degree is too small, the strength of the polyimide film tends to be inadequate when it is used as an alignment film, whereby alignment of liquid crystal tends to be unstable. On the other hand, if the polymerization degree is too large, the operation efficiency for forming a polyimide film is likely to be poor.

Accordingly, the polymerization degree of the product in this reaction is preferably from 0.05 to 5.0 dl/g (in N-methylpyrrolidone at a temperature of 30° C., concentration: 0.5 g/dl) as calculated as the reduced viscosity of the polyimide precursor solution.

The method for reacting and polymerizing the tetracarboxylic acid dianhydride with the primary diamine is not particularly limited. It is common to employ a method wherein the primary diamine is dissolved in an organic polar solvent such as N-methylpyrrolidone, N,N-dimethylacetamide or N,N-dimethylformamide, and the tetracarboxylic acid dianhydride is added and reacted to the solution to obtain a polyimide precursor, followed by dehydration for ring closure imide-conversion.

The reaction temperature at the time of reacting the tetracarboxylic acid dianhydride with the primary diamine to form a polyimide precursor, may be selected to be an optional temperature within a range of from −20° to 150° C., preferably from −5° to 100° C.

Further, this polyimide precursor is heated and dehydrated at a temperature of from 100° to 400° C., or subjected to chemical imide-conversion by means of a commonly employed imide-conversion catalyst such as triethylamine/acetic anhydride, to obtain a polyimide.

To use the polyimide of the present invention as an insulating film or a protective film for an electrical or electronic element, or as an alignment film for a liquid crystal display device, it is necessary to form a polyimide coating film in a uniform thickness on a substrate.

To form such a polyimide coating film, the polyimide precursor solution may usually be coated on a substrate as it is and heated for imide-conversion to form a polyimide coating film on the substrate. As the polyimide precursor solution to be used, the above-mentioned polymerization solution may be used as it is, or the formed polyimide precursor may be put into a large excess amount of water or a poor solvent such as methanol, for precipitation and recovery, and then it is re-dissolved in a solvent for use. The solvent for diluting the above polyimide precursor solution and/or the solvent for re-dissolving the polyimide precursor recovered by precipitation, is not particularly limited, so long as it is capable of dissolving the polyimide precursor.

Specific examples of such solvents include N-methylpyrrolidone, N,N-dimethylacetamide and N,N-dimethylformamide. These solvents may be used alone or in combination as a mixture.

Further, even a solvent which is in capable of providing a uniform solution by itself, may be incorporated within a range in which a uniform solution can be obtained.

The temperature for heating for imide-conversion on the substrate may be optionally selected within a range of from 100° to 400° C. However, particularly preferred is a temperature within a range of from 150° to 350° C.

On the other hand, in a case where the polyimide of the present invention is soluble in a solvent, the polyimide precursor obtained by reacting a tetracarboxylic acid dianhydride with a primary diamine, may be subjected to imide-conversion in a solution to obtain a polyimide solution. To convert the polyimide precursor to a polyimide in a solution, it is usual to employ a method whereby dehydration ring-closure is carried out by heating. The temperature for heating for dehydration ring-closure can be optionally selected within a range of from 150° to 350° C., preferably from 120° to 250° C.

As another method for converting the polyimide precursor to a polyimide, it is possible to carry out the ring closure chemically by means of a conventional catalyst for dehydration ring closure.

The polyimide solution thus obtained may used as it is, or it may be precipitated in a poor solvent such as methanol or ethanol, isolated and then re-dissolved in a proper solvent for use. The solvent for re-dissolving it, is not particularly limited so long as it is capable of dissolving the obtained polyimide. It may, for example, be 2-pyrrolidone, N-methylpyrrolidone, N-ethylpyrrolidone, N-vinylpyrrolidone, N,N-dimethylacetamide, N,N-dimethylformamide or γ-butyrolactone.

In addition, even a solvent which is in capable of dissolving the polyimide by itself, may be added to the above solvent within a range not to impair the solubility. Such a solvent may, for example, be ethyl cellosolve, butyl cellosolve, ethyl carbitol, butyl carbitol, ethyl carbitol acetate or ethylene glycol.

Further, for the purpose of improving the adhesion of the polyimide film to the substrate, it is preferred to add an additive such as a coupling agent to the obtained polyimide solution.

A polyimide coating film can be formed on the substrate by coating such a solution on the substrate and evaporating the solvent. The temperature in such a case may be at such a level that the solvent evaporates, and it is usually from 80° to 150° C.

In such a manner, a polyimide film having a thickness of from 200° to 3000 Å may be formed on a transparent substrate such as a glass sheet or a plastic film having a transparent electrode, and then the polyimide layer is subjected rubbing treatment to obtain a liquid crystal alignment film.

Now, the present invention will be described in further detail with reference to Examples. However, it should be understood that the present invention is by no means restricted to such specific Examples.

EXAMPLE 1

Preparation of 4-[3-(4-biphenyloxy)propoxy]-1,3-diaminobenzene

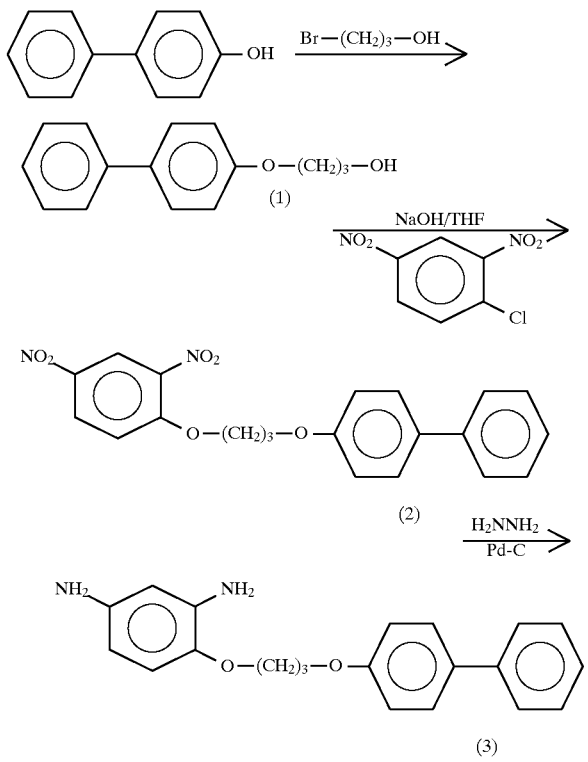

Into a 200 ml flask, 7.82 g (41.1 mmol) of 4-hydroxybiphenyl, 83 ml of ethanol, 6 g (43.2 mmol) of 3-bromo-1-propanol and a NaOH aqueous solution (1.73 g (43.2 mmol) of NaOH/6 ml of water) were sequentially added, and the mixture was heated and refluxed for 6.5 hours. To the reaction solution, 50 ml of water was added, whereupon precipitated crystals were collected by filtration and recrystallized from ethanol to obtain 4.0 g (yield: 43%) of 4-(3-hydroxypropoxy)biphenyl (1) as a colorless powder.

In a 200 ml flask, 3 g (13.1 mmol) of the obtained 4-(3-hydropropoxy)biphenyl (1) was dissolved in 47 ml of THF, and 578 mg (14.5 mmol) of NaOH was added thereto. The mixture was heated and refluxed for 2 hours. The reaction mixture was returned to room temperature, and a THF solution (15 ml) of 2.53 g (12.5 mmol) of 2,4-dinitrochlorobenzene, was dropwise added thereto. Then, the mixture was stirred overnight. The reaction mixture was poured into water and extracted with 300 ml of chloroform. The chloroform layer was washed with water and a saturated sodium chloride aqueous solution and then dried over anhydrous sodium sulfate. Further, the solvent was distilled off under reduced pressure, and the residue (4.43 g) was purified by silica gel column chromatography to obtain 3.93 g of a yellow powder. This powder was recrystallized from acetonitrile to obtain 2.55 g (yield: 49%) of yellow crystals. From the IR, NMR and MASS spectra, the crystals were found to be 4-[3-(4-biphenyloxy)propoxy]-1,3-dinitrobenzene (2) as the desired diamine precursor dinitro compound.

Into a 50 ml flask, 2 g (5.1 mmol) of the dinitro compound (2) and 27 ml of isopropyl alcohol were introduced, and the reaction system was flushed with nitrogen. Then, 170 mg (10.1 mmol) of 5% Pd—C powder was added thereto. Then, 1.7 ml of a 98% hydrazine aqueous solution was added thereto and stirred at 40° C. overnight. The Pd—C powder was filtered off, and the filtrate was washed with water and a saturated sodium chloride aqueous solution and then dried over anhydrous sodium sulfate. The solvent was distilled off under reduced pressure to obtain 1.67 g of a slightly yellow powder. This powder was recrystallized from benzene to obtain 1.42 g (yield: 84%) of slightly yellow crystals.

From the IR, NMR and MASS spectra, the crystals were found to be 4-[3-(4-biphenyloxy)propoxy]-1,3-diaminobenzene (3) as the desired diamine.

Melting point: 144° C.

Mass spectrum (m/e): 334(M$^+$)

$^1$H-NMR(CDCl$_3$, δ ppm): 2.30(2H,dd,CH$_2$), 3.60(4H,bs, NH$_2$), 4.10(2H,t,OCH$_2$), 4.20(2H,t,OCH$_2$), 6.10(1H,d, H$_{arom}$), 6.20(1H,s,H$_{arom}$), 6.80(1H,d,H$_{arom}$), 7.00(2H,d, H$_{arom}$), 7.32–7.60(7H,m,H$_{arom}$)

IR(KBr,cm$^{-1}$): 3438(NH$_2$), 3353(NH$_2$), 2959(CH$_2$), 2938 (CH$_2$), 2882(CH$_2$)

EXAMPLE 2

Preparation of 4-[8-(4-biphenyloxy)octyloxy]-1,3-diaminobenzene (6)

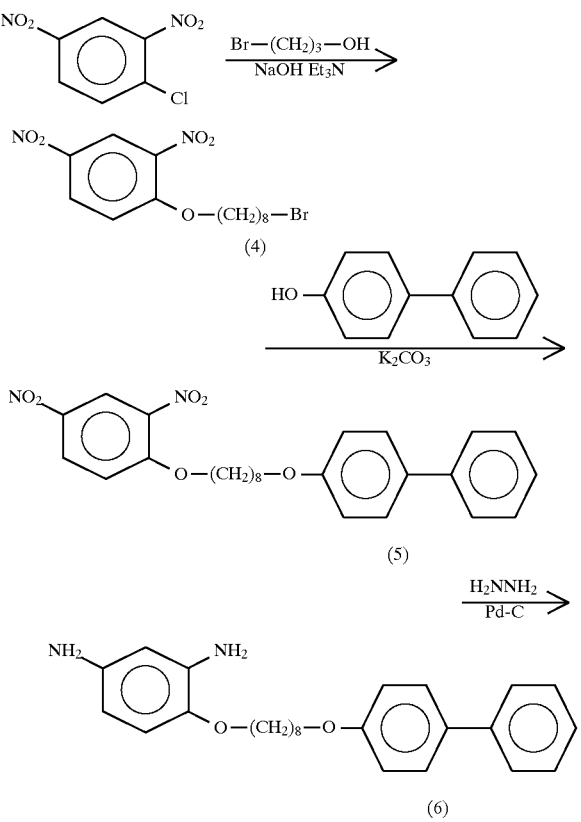

Into a 100 ml flask, 4.36 g (21.5 mmol) of 2,4-dinitrochlorobenzene, 5.0 g (23.9 mmol) of 8-bromooctanol, 14 ml of dimethylacetamide, 483 mg (4.8 mmol) of triethylamine and 1.05 g (26.3 mmol) of NaOH were added and stirred at 40° C. for 2.5 hours. The reaction mixture was poured into water and extracted with 300 ml of chloroform.

The chloroform layer was washed with water and a saturated sodium chloride aqueous solution and then dried over anhydrous sodium sulfate. Further, the solvent was distilled off under reduced pressure, and the residue was purified by silica gel column chromatography to obtain 3.90 g (yield: 59%) of 4-(8-bromooctyloxy)-1,3-dinitrobenzene (4) as a yellow oily substance.

Into a 200 ml flask, 3.90 g (10.4 mmol) of the dinitro compound (4), 1.98 g (10.4 mmol) of 4-hydroxyphenyl and 2.87 g (20.8 mmol) of anhydrous potassium carbonate were added, and the mixture was heated and refluxed for 15 hours. The solvent was distilled off under reduced pressure. Then, the reaction mixture was poured into water and extracted with chloroform. The chloroform layer was washed with water and a saturated sodium chloride aqueous solution and then dried over anhydrous sodium sulfate. Further, the solvent was distilled off under reduced pressure, and the residue (4.43 g) was purified by silica gel column chromatography to obtain 2.4 g of a yellow powder. The powder was recrystallized from acetonitrile to obtain 2.33 g (yield: 48%) of yellow crystals. From the IR, NMR and MASS spectra, the crystals were found to be 4-[8-(4-biphenyloxy)octyloxy]-1,3-dinitrobenzene (5) as the desired diamine precursor dinitro compound.

2 g (4.3 mmol) of the obtained dinitro compound (5), 152 mg (9 mmol) of 5% Pd—C powder, 24 ml of isopropanol and 1.7 ml of a 98% hydrazine aqueous solution were added and treated in the same manner as in Example 1 to obtain 1.72 g of a slightly yellow powder. This powder was recrystallized from benzene/hexane to obtain 1.56 g (yield: 90%) of dark yellow crystals. From the IR, NMR and MASS spectra, the crystals were found to be 4-[8-( 4-biphenyloxy)octyloxy]-1,3-diaminobenzene (6) as the desired diamine. The analytical results are shown below.

Melting point: 111° C.

Mass spectrum (m/e): 405(M$^+$)

$^1$H-NMR(CDCl$_3$, δ ppm): 1.30–1.90(12H,m,CH$_2$), 3.60 (4H,bs,NH$_2$), 4.10(2H,t,OCH$_2$), 4.20(2H,t,OCH$_2$), 6.10(1H, d,H$_{arom}$), 6.20(1H,s,H$_{arom}$), 6.80(1H,d,H$_{arom}$), 7.05(2H,d, H$_{arom}$), 7.30–7.60(7H,m,H$_{arom}$)

IR(KBr,cm$^{-1}$): 3466(NH$_2$), 3374(NH$_2$), 2931(CH$_2$), 2861 (CH$_2$)

EXAMPLE 3

Preparation of 4-[3-(4-cyanobiphenyl-4'-oxy)propoxy]-1,3-diaminobenzene (9)

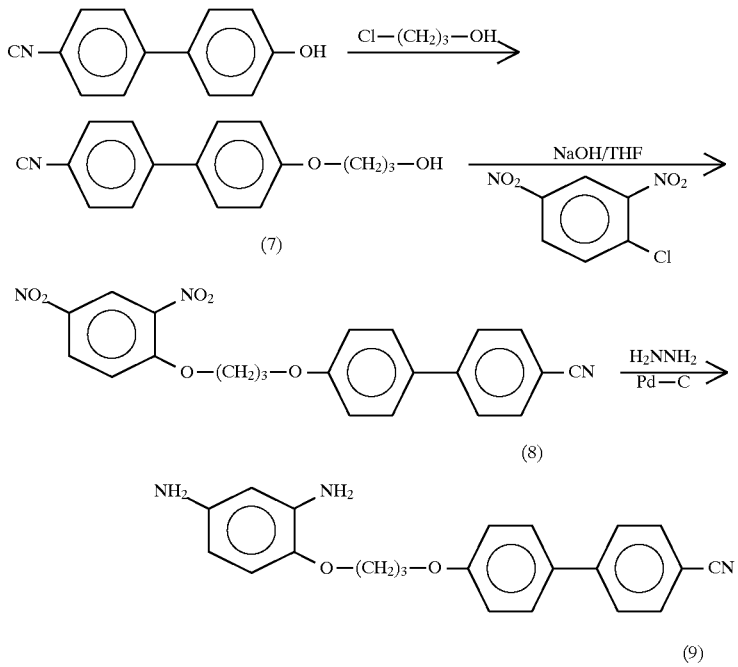

Into a 300 ml flask, 20 g (102.4 mmol) of 4-cyano-4'-hydroxybiphenyl, 140 ml of ethanol and a NaOH aqueous solution (7.48 g (132.2 mmol) of NaOH/40 ml of water) were added. The mixture was stirred at 80° C. for 10 minutes, and then 10.66 g (112.8 mmol) of 3-chloro-1-propanol was added thereto. The mixture was heated and refluxed for 18 hours. Ethanol was distilled off. Then, 300 ml of water was added to the reaction solution, and the mixture was neutralized with hydrochloric acid. Precipitated crystals were collected by filtration. Then, 1200 ml of toluene was added thereto, and the toluene layer was washed with water and a saturated sodium chloride aqueous solution and then dried over anhydrous sodium sulfate. Further, the solvent was distilled off under reduced pressure, and the residue was recrystallized from ethanol to obtain 5.34 g (yield: 21%) of 4-cyano-4'-(3-hydroxypropoxy)biphenyl (7) as colorless crystals.

Using 3.2 g (12.6 mmol) of 4-cyano-4'-(3-hydroxypropoxy)biphenyl (7), 40 ml of THF, 850 mg (15.2 mmol) of NaOH and 2.47 g (12.6 mmol) of 2,4-dinitrochorobenzene, synthetic treatment was carried out in the same manner as in Example 1 to obtain 2.76 g of a yellow powder. This powder was recrystallized from chloroform/hexane to obtain 2.14 g (yield: 40%) of slightly yellow crystals. From the IR, NMR and MASS spectra, the crystals were found to be 4-[3-(4-cyanobiphenyl-4'-oxy)propoxy]-1,3-dinitrobenzene (8) as the desired diamine precursor dinitro compound.

Using 1.6 g (3.8 mmol) of the dinitro compound (8), 21 ml of isopropyl alcohol, 128 mg (7.6 mmol) of 5% Pd—C powder and 1.1 ml of a 98% hydrazine aqueous solution, synthetic treatment was carried out in the same manner as in Example 1 to obtain a slightly yellow powder. This powder was dissolved in methylene chloride and precipitated with n-hexane for purification to obtain 1.25 g (yield: 91%) of yellow crystals. From the IR, NMR and MASS spectra, the crystals were found to be 4-[3-(4-cyanobiphenyl-4'-oxy)propoxy]-1,3-diaminobenzene (9) as the desired diamine. The analytical results are shown below.

Melting point: 126° C.

Mass spectrum (m/e): 359(M$^+$)

$^1$H-NMR(CDCl$_3$, δ ppm): 2.28(2H,dd,CH$_2$), 3.60(4H,bs,NH$_2$), 4.13 (2H,t,OCH$_2$), 4.23 (2H,t,OCH$_2$), 6.04(1H,d,H$_{arom}$), 6.13(1H,s,H$_{arom}$), 6.66(1H,d,H$_{arom}$), 7.02(2H,d,H$_{arom}$), 7.52(2H,d,H$_{arom}$), 7.64(2H,d,H$_{arom}$), 7.69(2H,d,H$_{arom}$)

IR(KBr,cm$^{-1}$): 3438(NH$_2$), 3360(NH$_2$), 2940(CH$_2$), 2875 (CH$_2$), 2221(CN)

EXAMPLE 4

Preparation of 4-[12-(4-cyanobiphenyl-4'-oxy)dodecyloxy]-1,3-diaminobenzene (12)

mmol) of anhydrous potassium carbonate, 189 mg (1.1 mmol) of potassium iodide and 110 ml of acetonitrile, synthetic treatment was carried out in the same manner as in Example 2.

5.0 g of the obtained yellow powder was recrystallized from acetonitrile to obtain 4.40 g (yield: 71%) of slightly yellow crystals. From the IR, NMR and MASS spectra, the crystals were found to be 4-[12-(4-cyanobiphenyl-4'-oxy)dodecyloxy]-1,3-dinitrobenzene (11) as the desired diamine precursor dinitro compound.

3 g (5.5 mmol) of the obtained dinitro compound (11), 184 mg (11 mmol) of 5% Pd—C powder, 29 ml of isopropanol and 1.8 ml of a 98% hydrazine aqueous solution were added and treated in the same manner as in Example 1 to obtain 2.66 g of a colorless powder. This powder was dissolved in methylene chloride and precipitated with n-hexane for purification to obtain 1.72 g (yield: 64%) of colorless crystals. From the IR, NMR and MASS spectra, the crystals were found to be 4-[12-(4-cyanobiphenyl-4'-oxy)dodecyloxy]-1,3-diaminobenzene (12) as the desired diamine. The analytical results are shown below.

Melting point: 129° C.

Mass spectrum (m/e): 486(M$^+$)

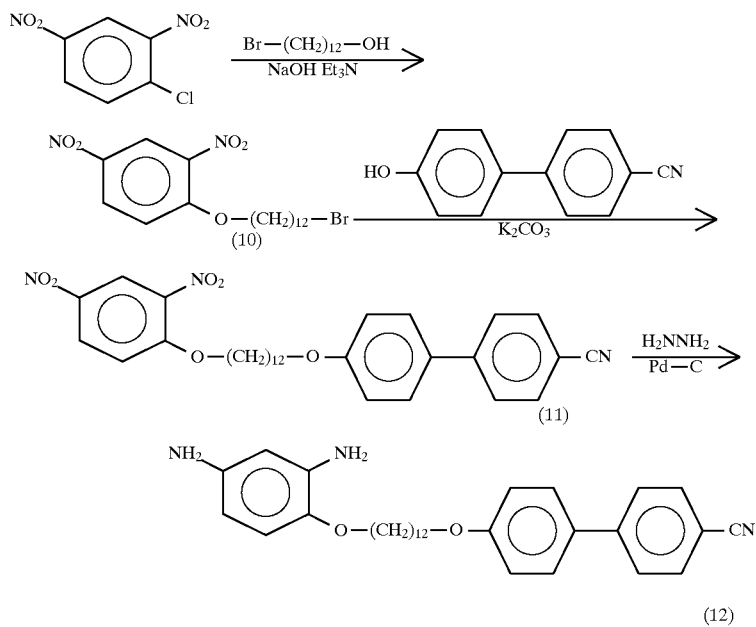

Using 3.82 g (18.9 mmol) of 2,4-dinitrochlorobenzene, 5 g (18.9 mmol) of 12-bromododecanol, 12 ml of dimethylacetamide, 382 mg (3.8 mmol) of triethylamine and 905 mg (22.6 mmol) of NaOH, synthetic treatment was carried out in the same manner as in Example 2.

The obtained yellow powder was recrystallized from acetonitrile/water to obtain 4.91 g (yield: 60%) of 4-[12-bromododecyloxy]-1,3-dinitrobenzene (10) as colorless powder.

Using 4.9 g (11.4 mmol) of the dinitro compound (10), 2.2 g (11.4 mmol) of 4-cyano-4'-hydroxybiphenyl, 3.14 g (22.7

$^1$H-NMR(CDCl$_3$, δ ppm): 1.10–1.85(20H,m,CH$_2$), 3.70 (4H,bs,NH$_2$), 3.90(2H,t,OCH$_2$), 4.00(2H,t,OCH$_2$), 6.05(1H, d,H$_{arom}$), 6.15(1H,s,H$_{arom}$), 6.60(1H,d,H$_{arom}$), 7.00(2H,d, H$_{arom}$), 7.53(2H,d,H$_{arom}$), 7.65(2H,d,H$_{arom}$), 7.70(2H,d, H$_{arom}$)

IR(KBr,cm$^{-1}$): 3473(NH$_2$), 3452(NH$_2$), 3381(NH$_2$), 3360 (NH$_2$), 2931(CH$_2$), 2924(CH$_2$), 2854(CH$_2$), 2854(CH$_2$), 2221(CN)

EXAMPLE 5

Preparation of 4-[6-(4-methoxybiphenyl-4'-oxy)hexyloxy]-1,3-diaminobenzene (15)

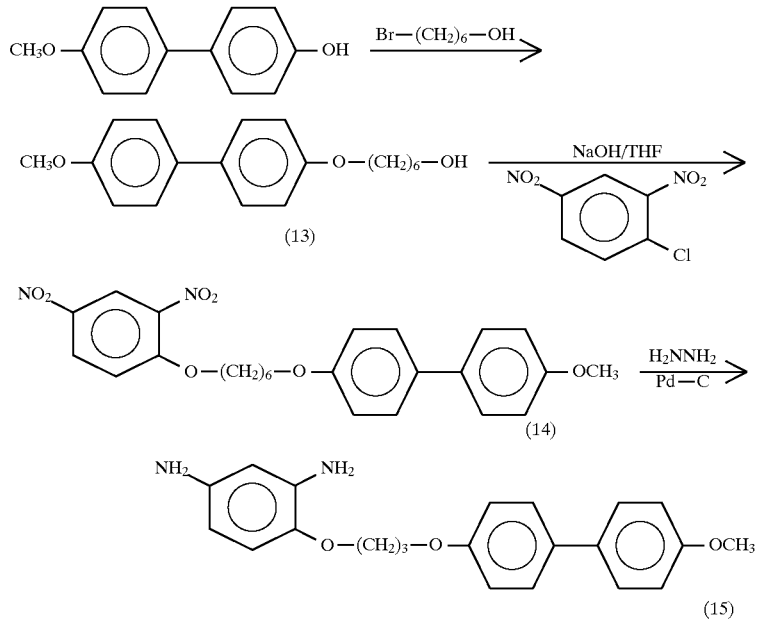

Using 5 g (25 mmol) of 4-methoxy-4'-hydroxybiphenyl, 50 ml of ethanol, 4.52 g (25 mmol) of 6-bromo-1-hexanol and a NaOH aqueous solution (1.05 g (26.2 mmol) of NaOH/3 ml of water), synthetic treatment was carried out in the same manner as in Example 1. The obtained crystals were recrystallized from methanol to obtain 5.71 g (yield: 76%) of 4-methoxy-4'-(6-hydroxyhexyloxy)biphenyl (13) as colorless crystals.

Using 5 g (16.6 mmol) of the obtained 4-methoxy-4'-(6-hydroxyhexyloxy)biphenyl (13), 80 ml of THF, 1.12 mg (20 mmol) of NaOH and 3.20 g (15.8 mmol) of 2,4-dinitrochlorobenzene, synthetic treatment was carried out in the same manner as in Example 1. The obtained yellow powder was recrystallized from acetonitrile/water to obtain 2.75 g (yield: 35%) of slightly yellow crystals. From the IR, NMR and MASS spectra, the crystals were found to be 4-[6-(4-methoxybiphenyl-4'-oxy)hexyloxy]-1,3-dinitrobenzene (14) as the desired diamine precursor dinitro compound.

Using 3.5 g (7.5 mmol) of the dinitro compound (14), 35 ml of isopropyl alcohol, 251 mg (15.1 mmol) of 5% Pd—C powder and 1.5 ml of a 98% hydrazine aqueous solution, synthetic treatment was carried out in the same manner as in Example 1. The obtained gray powder was recrystallized from benzene to obtain 2.5 g (yield: 82%) of colorless crystals. From the IR, NMR and MASS spectra, the crystals were found to be 4-[6-(4-methoxybiphenyl-4'-oxy)hexyloxy]-1,3-diaminobenzene (15) as the desired diamine. The analytical results are shown below.

Melting point: 133° C.

Mass spectrum (m/e): 407($M^+$)

$^1$H-NMR(CDCl$_3$, δ ppm): 1.53(4H,m,CH$_2$), 1.82(4H,m,CH$_2$), 3.55(4H,bs,NH$_2$), 3.83(3H,S,OCH$_3$), 3.90(2H,t,OCH$_2$), 4.00(2H,t,OCH$_2$), 6.04(1H,d,H$_{arom}$), 6,12(1H,s,H$_{arom}$), 6.60(1H,d,H$_{arom}$) 6.93(2H,d,H$_{arom}$), 6.95(2H,d,H$_{arom}$), 7.45(2H,d,H$_{arom}$), 7.47(2H,d,H$_{arom}$)

IR(KBr,cm$^{-1}$): 3445(NH$_2$), 3409(NH$_2$), 3325(NH$_2$), 2931(CH$_2$), 2854(CH$_2$)

EXAMPLE 6 preparation of 4-[6-(4-methoxybiphenyl-4'-oxy)dodecyloxy]-1,3-diaminobenzene (17)

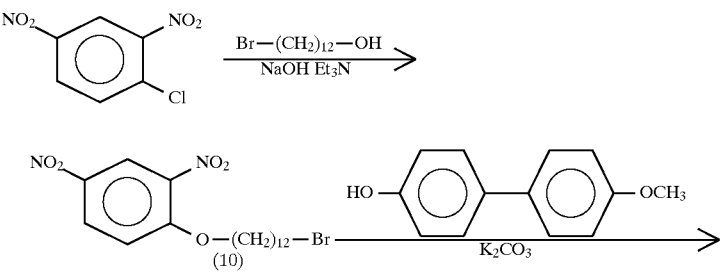

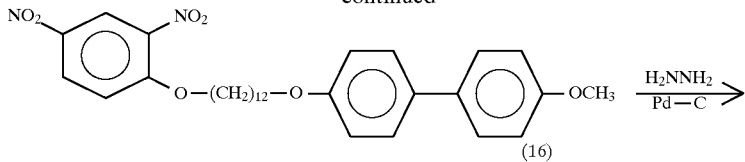

(16)

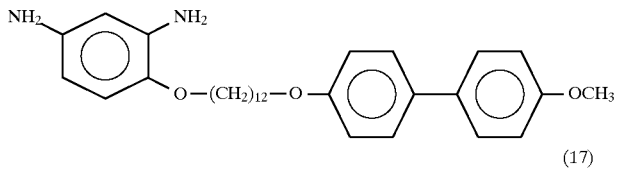

(17)

Using 5 g (11.6 mmol) of the dinitro compound (10) obtained in Example 4, 2.32 g (11.6 mmol) of 4-methoxy-4'-hydroxybiphenyl, 3.20 g (23.2 mmol) of anhydrous potassium carbonate, 192 mg (1.2 mmol) of potassium iodide and 116 ml of acetonitrile, synthetic treatment was carried out in the same manner as in Example 2. 4.92 g of the obtained yellow crystals were recrystallized from ethyl acetate to obtain 3.45 g (yield: 54%) of slightly yellow crystals. From the IR, NMR and MASS spectra, the crystals were found to be 4-[6-(4-methoxybiphenyl-4'-oxy)dodecyloxy]-1,3-dinitrobenzene (16) as the desired diamine precursor dinitro compound.

500 mg (0.9 mmol) of the obtained dinitro compound, 31 mg (1.82 mmol) of 5% Pd—C powder, 7 ml of isopropanol and 0.2 ml of a 98% hydrazine aqueous solution were added and treated in the same manner as in Example 1 to obtain 2.66 g of a colorless powder. This powder was recrystallized from benzene to obtain 400 mg (yield: 93%) of colorless crystals. From the IR, NMR and MASS spectra, the crystals were found to be 4-[6-(4-methoxybiphenyl-4'-oxy)dodecyloxy]-1,3-diaminobenzene (17) as the desired diamine. The analytical results are shown below.

Melting point: 129° C.

Mass spectrum (m/e): 475(M$^+$)

$^1$H-NMR(CDCl$_3$, δ ppm): 1.19–1.84(20H,m,CH$_2$), 3.54 (4H,bs,NH$_2$), 3.84(3H,s,OCH$_3$), 3.90(2H,t,OCH$_2$), 3.99(2H, t,OCH$_2$), 6.04(1H,d,H$_{arom}$), 6.13(1H,s,H$_{arom}$), 6.62(1H,d, H$_{arom}$), 6.96(4H,m,H$_{arom}$), 7.46(4H,m,H$_{arom}$)

IR(KBr,cm$^{-1}$): 3465(NH$_2$), 3374(NH$_2$), 2931(CH$_2$), 2917 (CH$_2$), 2847(CH$_2$)

EXAMPLE 7

Preparation of 4-[3-(4-fluorobiphenyl-4'-oxy)propoxy]-1,3-diaminobenzene (20)

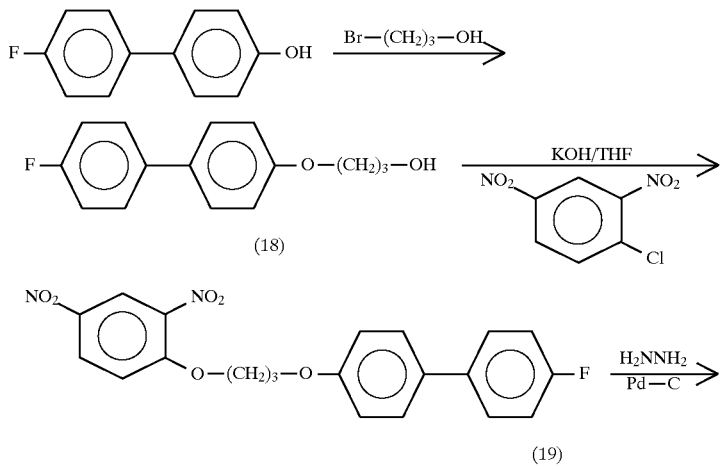

(18)

(19)

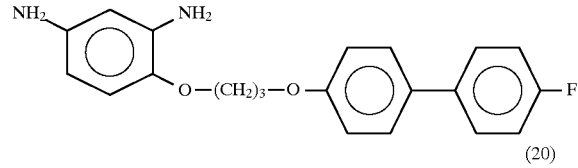

(20)

Using 2.8 g (14.9 mmol) of 4-fluoro-4'-hydroxybiphenyl, 50 ml of acetonitrile, 2.17 g (15.6 mmol) of 3-bromopropanol and 4.11 g (30 mmol) of anhydrous potassium carbonate, synthetic treatment was carried out in the same manner as in Example 2. The obtained colorless powder was recrystallized from benzene/n-hexane to obtain 3.26 g (yield: 89%) of 4-fluoro-4'-(3-hydroxypropoxy) biphenyl (18) as a colorless powder.

Using 3 g (12.2 mmol) of the obtained 4-fluoro-4'-(3-hydroxypropoxy)biphenyl (18), 44 ml of THF, 820 mg (14.6 mmol) of KOH and 2.47 g (12.2 mmol) of 2,4-dinitrochlorobenzene, synthetic treatment was carried out in the same manner as in Example 1. The obtained yellow powder was recrystallized from acetonitrile to obtain 1.40 g (yield: 28%) of yellow crystals. From the IR, NMR and MASS spectra, the crystals were found to be 4-[3-(4-fluorobiphenyl-4'-oxy)propoxy]-1,3-dinitrobenzene (19) as the desired diamine precursor dinitro compound.

Using 850 mg (2.1 mmol) of the dinitro compound (19), 10 ml of isopropyl alcohol, 75 mg (4.1 mmol) of 5% Pd—C powder and 0.8 ml of a 98% hydrazine aqueous solution, synthetic treatment was carried out in the same manner as in Example 1. The obtained colorless powder was recrystallized from benzene/n-hexane to obtain 660 mg (yield: 91%) of colorless crystals. From the IR, NMR and MASS spectra, the crystals were found to be 4-[3-(4-fluorobiphenyl-4'-oxy)propoxy]-1,3-diaminobenzene (20) as the desired diamine. The analytical results are shown below.

Melting point: 116° C.

Mass spectrum (m/e): 352($M^+$)

$^1$H-NMR(CDCl$_3$, δ ppm): 2.25(2H,dd,CH$_2$), 3.60(4H,bs, NH$_2$), 4.20(2H,t,OCH$_2$), 4.30(2H,t,OCH$_2$), 6.12(1H,d, H$_{arom}$), 6.20(1H,s,H$_{arom}$), 6.76(1H,d,H$_{arom}$), 6.96(2H,d, H$_{arom}$), 7.10(2H,t,H$_{arom}$), 7.48(4H,m,H$_{arom}$)

IR(KBr,cm$^{-1}$): 3482(NH$_2$), 3398(NH$_2$), 3321(NH$_2$), 2940(CH$_2$), 2875(CH$_2$), 1227(F)

EXAMPLE 8

Preparation of 4-[3-(4-trifluoromethoxybiphenyl-4'-oxy)propoxy]-1,3-diaminobenzene (23)

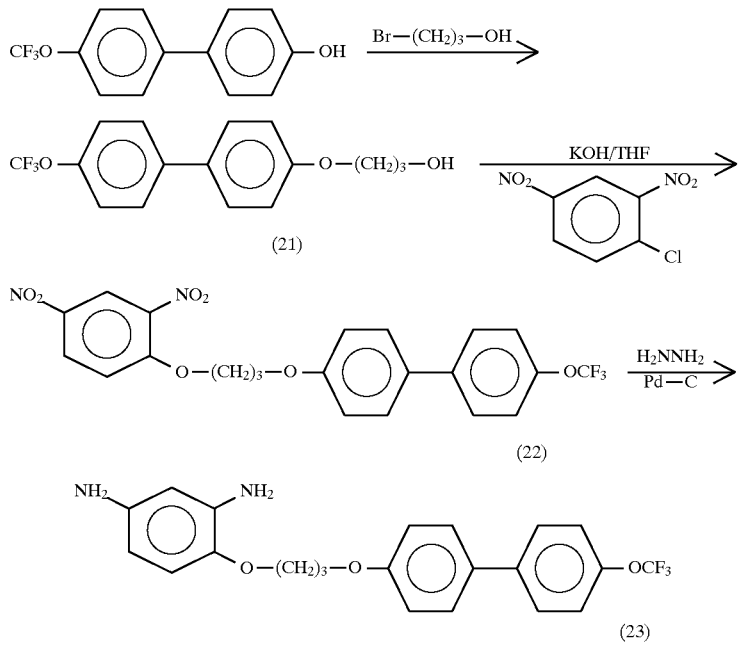

Using 3.5 g (13.8 mmol) of 4-trifluoromethoxy-4'-hydroxybiphenyl, 45 ml of acetonitrile, 2.01 g (14.5 mmol) of 3-bromo-1-propanol and 3.81 g (27.5 mmol) of anhydrous potassium carbonate, synthetic treatment was carried out in the same manner as in Example 2. The obtained gray powder was recrystallized from benzene/n-hexane to obtain 3.52 g (yield: 82%) of 4-trifluoromethoxy-4'-(3-hydroxypropoxy)biphenyl (21) as a colorless powder.

Using 3 g (9.6 mmol) of the obtained 4-trifluoromethoxy-4'-(3-hydroxypropoxy)biphenyl (21), 35 ml of THF, 647 mg (11.5 mmol) of KOH and 1.95 g (9.6 mmol) of 2,4-dinitrochlorobenzene, synthetic treatment was carried out in the same manner as in Example 1. The obtained yellow powder was recrystallized from acetonitrile/water to obtain 1.72 g (yield: 37%) of a colorless powder. From the IR, NMR and MASS spectra, the crystals were found to be 4-[3-(4-trifluoromethoxybiphenyl-4'-oxy)propoxy]-1,3-dinitrobenzene (22) as the desired diamine precursor dinitro compound.

Using 1.4 g (2.9 mmol) of the dinitro compound (22), 14 ml of isopropyl alcohol, 98 mg (5.9 mmol) of 5% Pd—C powder and 1.2 ml of 98% hydrazine aqueous solution, synthetic treatment was carried out in the same manner as in Example 1. The obtained colorless powder was recrystallized from benzene/n-hexane to obtain 1.11 g (yield: 90%) of colorless crystals. From the IR, NMR and MASS spectra, the crystals were found to be 4-[3-(4-trifluoromethoxybiphenyl-4'-oxy)propoxy]-1,3-diaminobenzene (23) as the desired diamine. The analytical results are shown below.

Melting point: 117° C.

Mass spectrum (m/e): 418($M^+$)

$^1$H-NMR(CDCl$_3$, δ ppm): 2.30(2H,dd,CH$_2$), 3.55(4H,bs, NH$_2$), 4.15(2H,t,OCH$_2$), 4.25(2H,t,OCH$_2$), 6.00(1H,d, H$_{arom}$), 6.08(1H,s,H$_{arom}$), 6.70(1H,d,H$_{arom}$), 6.90(2H,d, H$_{arom}$), 7.06(2H,d,H$_{arom}$), 7.35(2H,d,H$_{arom}$), 7.45(2H,d, H$_{arom}$)

IR(KBr,cm$^{-1}$): 3466(NH$_2$), 3395(NH$_2$), 3374(NH$_2$), 2960(CH$_2$), 2938(CH$_2$), 2882(CH$_2$), 1300–1166(OCF$_3$)

EXAMPLE 9

Preparation of 5-[6-(4-cyanobiphenyl-4'-oxy)hexyl]-1,3-diaminobenzoate (26)

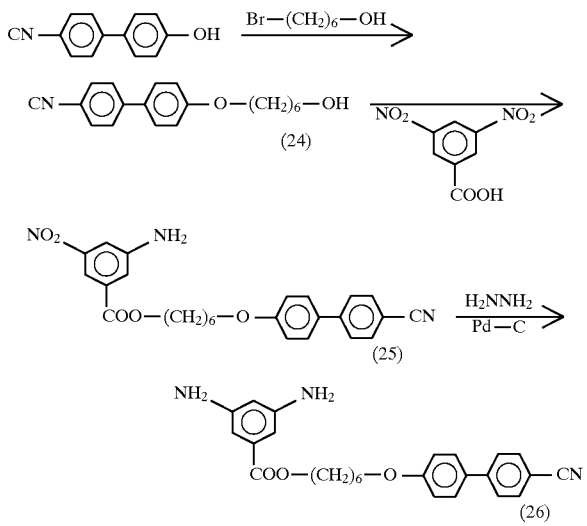

Using 5 g (25.6 mmol) of 4-cyano-4'-hydroxybiphenyl, 85 ml of acetonitrile, 4.63 g (25.6 mmol) of 6-bromohexanol and 7.09 g (51.2 mmol) of anhydrous potassium carbonate, synthetic treatment was carried out in the same manner as in Example 2. The obtained gray powder was recrystallized from methanol to obtain 3.6 g (yield: 48%) of 4-cyano-4'-(6-hydroxyhexyloxy)biphenyl (24) as a colorless powder.

Into a 100 ml flask, 3 g (10.2 mmol) of the obtained 4-cyano-4'-(6-hydroxyhexyloxy)biphenyl (24), 40 ml of methylene chloride and 1.96 g (9.2 mmol) of 3,5-dinitrobenzoic acid were added. Then, 113 mg (0.92 mmol) of 4-dimethylaminopyridine and 1.9 g (9.2 mmol) of dicyclohexylcarbodiimide were added thereto, and the mixture was stirred overnight. Precipitated crystals were collected by filtration and dissolved in methylene chloride. The methylene chloride layer was washed with water and a saturated sodium chloride aqueous solution and then dried over anhydrous sodium sulfate. Further, the solvent was distilled off under reduced pressure, and the residue was purified by silica gel column chromatography to obtain 2.70 g of a yellow powder. This powder was recrystallized from acetonitrile to obtain 2.0 g (yield: 44%) as yellow crystals. From the IR, NMR and MASS spectra, the crystals were found to be 5-[6-(4-cyanobiphenyl-4'-oxy)hexyl]-1,3-dinitrobenzoate (25) as the desired diamine precursor dinitro compound.

Using 1.5 g (3.1 mmol) of the dinitro compound (25), 16 ml of isopropyl alcohol, 102 mg (6.1 mmol) of 5% Pd—C powder and 1.0 ml of a 98% hydrazine aqueous solution, synthetic treatment was carried out in the same manner as in Example 1. The obtained yellow powder was dissolved in methylene chloride and then precipitated with n-hexane for purification to obtain 790 mg (yield: 60%) as yellow crystals. From the IR, NMR and MASS spectra, the crystals were found to be 5-[6-(4-cyanobiphenyl-4'-oxy)hexyl]-1,3-diaminobenzoate (26) as the desired diamine. The analytical results are shown below.

Melting point: 115° C.

Mass spectrum (m/e): 430($M^+$)

$^1$H-NMR(CDCl$_3$, δ ppm): 1.40–2.20(8H,m,CH$_2$), 3.60 (4H,bs,NH$_2$), 4.30(2H,t,OCH$_2$), 4.50(2H,t,OCH$_2$), 6.20(1H, s,H$_{arom}$), 6.80 (2H,s,H$_{arom}$), 7.04(2H,d,H$_{arom}$), 7.52(2H,d, H$_{arom}$), 7 66(2H,d,H$_{arom}$), 7.72(2H,d,H$_{arom}$)

IR(KBr,cm$^{-1}$): 3466(NH$_2$), 3360(NH$_2$), 2930(CH$_2$), 2880 (CH$_2$), 2228(CN)

EXAMPLE 10

Preparation of p-trans-4-pentylcyclohexylphenyl 4-(6-(1,3-diaminophenyl-5-carbonyl) hexyloxylbenzoate (30)

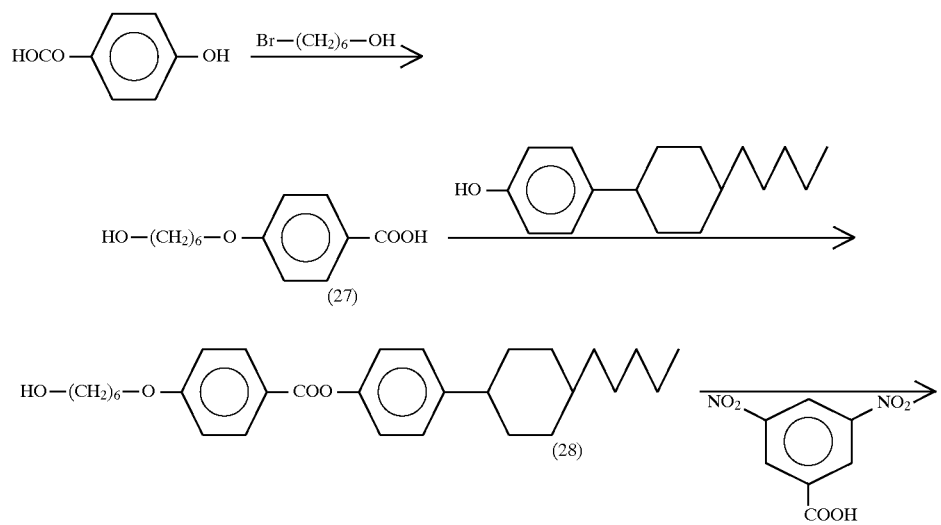

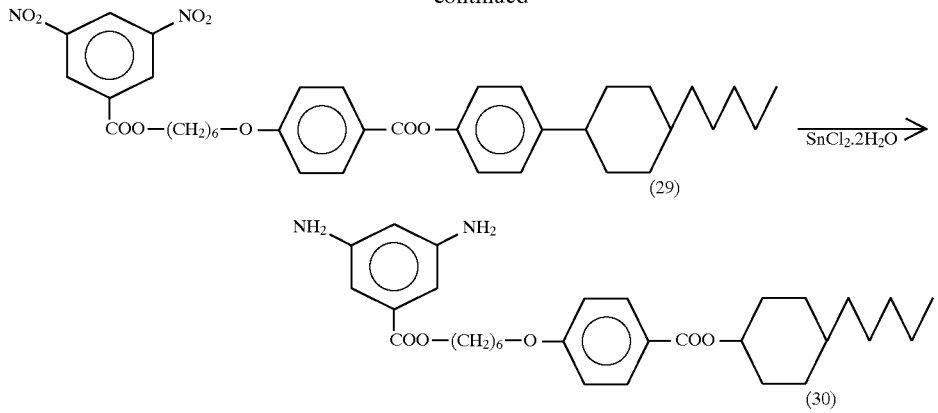

2 g (8.4 mmol) of 4-(6-hydroxyhexyloxy)benzoate (27) prepared in accordance with a literature (H. Ringsdorf Makromol. Chem. 183, 2311 (1981)) and 2.28 g (9.2 mmol) of p-trans-4-pentylcyclohexylphenol were suspended in 60 ml of methylene chloride, and 102 mg (0.8 mmol) of 4-dimethylaminopyridine and 1.9 g (9.2 mmol) of dicyclohexylcarbodiimide were added thereto. The mixture was stirred overnight. The reaction mixture was added to 200 ml of methylene chloride, and insolubles were filtered off. Then, filtrate was washed with 1N hydrochloric acid and a saturated sodium chloride aqueous solution and then dried over anhydrous sodium sulfate. Further, the solvent was distilled off under reduced pressure, and the residue was purified by silica gel column chromatography to obtain a colorless powder. This powder was recrystallized from methanol to obtain 2.26 g (yield: 58%) of p-trans-4-pentylcyclohexylphenyl 4-(6-hydroxyhexyloxy)benzoate (28).

2 g (4.3 mmol) of the obtained p-trans-4-pentylcyclohexylphenyl 4-(6-hydroxyhexyloxy)benzoate (28) and 826 mg (3.9 mmol) of 3,5-dinitrobenzoic acid were suspended in 15 ml of methylene chloride. Then, 50 mg (0.4 mmol) of 4-dimethylaminopyridine and 883 mg (4.3 mmol) of dicyclohexylcarbodiimide were added thereto, and the mixture was stirred overnight. To the reaction mixture, 100 ml of methylene chloride was added. Insolubles were filtered off, and the filtrate was washed with 1N hydrochloric acid and a saturated sodium chloride aqueous solution and then dried over anhydrous sodium sulfate. Further, the solvent was distilled off under reduced pressure, and the residue was purified by silica gel column chromatography to obtain a colorless powder. This powder was recrystallized from acetonitrile to obtain 1.45 g (yield: 56%) of a colorless powder. From the IR, NMR and MASS spectra, the crystals were found to be p-trans-4-pentylcyclohexylphenyl 4-[6-(1,3-dinitrophenyl-5-carbonyloxy)hexyloxy]benzoate (29).

661 mg (1 mmol) of the obtained dinitro compound (29) was dissolved in 3 ml of 1,4-dioxane. Then, 1.51 g (6.7 mmol) of tin chloride dihydrate and 1.51 g of concentrated hydrochloric acid were added thereto. The mixture was stirred at 30° C. for 3 hours. The obtained reaction product was poured into water and neutralized with a 50% NaOH aqueous solution. Then, precipitated crystals were collected by filtration and washed with water. The obtained colorless powder was recrystallized from acetonitrile/benzene to obtain 305 mg (yield: 51%) of a colorless powder.

From the IR, NMR and MASS spectra, the crystals were found to be p-trans-4-pentylcyclohexylphenyl 4-[6-(1,3-diaminophenyl-5-carbonyloxy)hexyloxy]benzoate (30). The analytical results are shown below.

Melting point: 151° C.

Mass spectrum (m/e): 601(M$^+$)

$^1$H-NMR(CDCl$_3$, δ ppm): 0.90–2.30(27H,CH$_2$,CH$_3$), 2.50(2H,t,H$_{ax}$), 3.66(4H,bs,NH$_2$), 4.20(2H,t,OCH$_2$), 4.50 (2H,t,OCH$_2$), 6.20(1H,s,H$_{arom}$), 6 78(2H,s,H$_{arom}$), 6.99(2H, d,H$_{arom}$) 7.12(2H,d,H$_{arom}$), 7.25(2H,d,H$_{arom}$), 8.12(2H,d, H$_{arom}$)

IR(KBr,cm$^{-1}$): 3423(NH$_2$), 3353(NH$_2$), 2924(CH$_2$), 2854 (CH$_2$), 1722(CO), 1694(CO)

EXAMPLE 11

1 g (3.0 mmol) of the diamine (3) obtained in Example 1 and 0.586 g (0.3 mol) of 1,2,3,4-cyclobutanetetracarboxylic acid dianhydride were dissolved in 13.4 g of N-methylpyrrolidone and stirred at 20° C. for 4 hours for a polycondensation reaction to obtain a polyimide precursor solution.

The reduced viscosity of the obtained polyimide precursor was 0.58 dl/g (concentration: 0.5 g/dl, in NMP, 30° C.).

This solution was coated on a glass substrate and heat-treated at 250° C. for one hour to form a uniform polyimide coating film.

The obtained coating film was subjected to IR measurement and found to be a polyimide containing a biphenyl group.

EXAMPLES 12 to 17

Using the diamines obtained in Examples 2 to 7, polyimide precursor solutions were prepared in the same manner as in Example 11. The reduced viscosities (concentration: 0.5 g/dl in NMP, 30° C.) of the obtained polyimide precursors were as shown in Table 1. Further, IR measurements were conducted in the same manner as in Example 11, and the coating films were found to be polyimides having cyclic groups corresponding to the respective diamines.

EXAMPLE 18

Using the diamine obtained in Example 8, a polyimide precursor solution was prepared in the same manner as in Example 11. The reduced viscosity (concentration: 0.5 g/dl in NMP, 30° C.) of the obtained polyimide precursor was as shown in Table 1. To 2 g of this solution, 4.66 g of N-methylpyrrolidone was added. Then, 0.33 g of acetic anhydride and 0.16 g of pyridine were added thereto. The mixture was stirred at room temperature for one hour and at 40° C. for 3 hours. The obtained solution was put into 250 ml of methanol, and precipitated crystals were collected by filtration and dried.

The obtained powder was subjected to IR measurement and found to be a polyimide containing a trifluoromethoxy-biphenyl group.

EXAMPLES 19 and 20

Using the diamines obtained in Examples 9 to 10, polyimide precursor solutions were prepared in the same manner as in Example 11. The reduced viscosities (concentration: 0.5 g/dl in NMP, 30° C.) of the obtained polyimide precursors were as shown in Table 1. Further, IR measurements were conducted in the same manner as in Example 11, and they were found to be polyimides having cyclic groups corresponding to the respective diamines.

TABLE 1

| Example | Diamine No. (Example No.) | Reduced viscosity ($\eta sp/c$) dl/g |
|---|---|---|
| 11 | (3) (Example 1) | 0.58 |
| 12 | (6) (Example 2) | 0.79 |
| 13 | (9) (Example 3) | 0.32 |
| 14 | (12) (Example 4) | 0.32 |
| 15 | (15) (Example 5) | 0.80 |
| 16 | (17) (Example 6) | 0.39 |
| 17 | (20) (Example 7) | 0.32 |
| 18 | (23) (Example 8) | 0.66 |
| 19 | (26) (Example 9) | 0.56 |
| 20 | (30) (Example 10) | 0.66 |

REFERENCE EXAMPLE

The polyimide precursor solutions obtained in Examples 13 and 15 were respectively coated on glass substrates and subjected to heat treatment at a predetermined temperature to form polyimide coating films. Then, water repellency of the polyimide surface, and the alignment properties and the tilt angles of liquid crystals, when used as liquid crystal alignment films, were measured. The results are shown in Table 2.

Evaluation of the water repellency

The polyimide precursor solution was diluted with N-methylpyrrolidone to obtain a solution having a resin concentration of 6%. The solution was spin-coated at 3500 rpm on a glass substrate and heat-treated at 80° C. for 10 minutes and 180° C. for one hour to form a uniform polyimide coating film, whereupon the contact angles of water and methylene iodide on the coating film were measured, and the surface energy of the polyimide was calculated by the Fowkes formula.

Evaluation of the tilt angle

The polyimide precursor solution was diluted with N-methylpyrrolidone to obtain a solution having a resin concentration of 6%. The solution was spin-coated at 3500 rpm on a glass substrate provided with a transparent electrode and heat-treated at 80° C. for 10 minutes and 250° C. for one hour to form a uniform polyimide coating film. This coating film was rubbed with a cloth. Then, a pair of substrates subjected to such rubbing treatment, were assembled with a spacer of 23 μm interposed therebetween, so that the respective rubbing directions were in parallel with each other, and a liquid crystal (ZLI-2293, manufactured by Merck Co.) was injected into the space to obtain a cell having a homogeneous alignment.

With respect to this cell, the uniformity of the liquid crystal alignment was confirmed under a polarized microscope, and then the tilt angle was measured by a magnetic field capacity method.

TABLE 2

| Polyimide (Example) | Diamine (Example) | Surface energy (dyn/cm) | Tilt angle (°) |
|---|---|---|---|
| 13 | 3 | 52 | 15 |
| 15 | 5 | 49 | 16 |

In each cell, flawless uniform alignment was observed, and a large tilt angle was obtained.

The diaminobenzene derivative of the present invention is easy to produce, and by synthesizing a polyimide having a structure similar to a liquid crystal molecule by using this derivative as one of the starting materials, it is possible to modify the surface properties of the polyimide, such as water repellency. Further, in the case of a polyimide for an alignment film for a liquid display device, it is possible to align liquid crystal uniformly and to increase the tilt angle.

What is claimed is:

1. A diaminobenzene derivative of the formula (I)

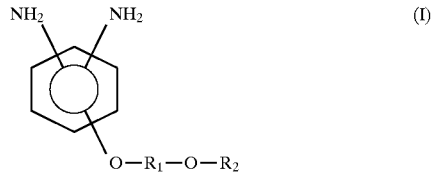

wherein $R_1$ is a $C_{2-22}$ straight chain alkylene group, and $R_2$ is a cyclic group selected from the group consisting of an aliphatic ring and substituted forms of such rings, with a substituent selected from the group consisting of an alkyl group, a halogen atom, a methoxy group, a trifluoromethoxy group, a nitro group, an amino group, a cyano group, an azo group, a formyl group, an acetyl group and an acetoxy group.

2. A diaminobenzene derivative of the formula (I)

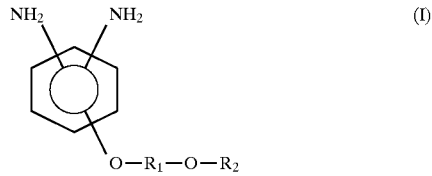

wherein $R_1$ is a $C_{2-22}$ straight chain alkylene group, and $R_2$ is a cyclic group selected from the group consisting of an aromatic ring substituted with a substituent selected from the group consisting of an alkyl group, a halogen atom, a methoxy group, a trifluoromethoxy group, a nitro group, a cyano group, an azo group, a formyl group, an acetyl group and an acetoxy group.

3. The diaminobenzene derivative according to claim 1, wherein said aliphatic ring is selected from the group consisting of cyclohexyl, bicyclohexyl, tercyclohexyl and phenylcyclohexyl.

4. The diaminobenzene derivative according to claim 1, wherein said aliphatic ring is cyclohexyl.

5. The diaminobenzene derivative according to claim 1, wherein $R_2$ in the formula (I) is a cyclic group substituted by a substituent selected from the group consisting of a halogen atom, a methoxy group, a trifluoromethoxy group, a cyano group and an alkyl group.

6. The diaminobenzene derivative according to claim 2, wherein said aromatic ring is selected from the group consisting of benzene, biphenyl, and terphenyl.

7. The diaminobenzene derivative according to claim 2, wherein said aromatic ring is benzene.

8. The diaminobenzene derivative according to claim 2, wherein $R_2$ in the formula (I) is a cyclic group substituted by a substituent selected from the group consisting of a halogen atom, a methoxy group, a trifluoromethoxy group, a cyano group and an alkyl group.

9. A diaminobenzene derivative, which is 4-[3-(4-biphenyloxy)propoxy)-1,3-diaminobenzene.

* * * * *